(12) United States Patent
Sandee et al.

(10) Patent No.: US 7,790,923 B2
(45) Date of Patent: Sep. 7, 2010

(54) PROCESS FOR THE PRODUCTION OF PHOSPHOROUS COMPOUNDS

(75) Inventors: Albertus Jacobus Sandee, Utrecht (NL); Alida Maria Van Der Burg, Castricum (NL); Joost Nicolaas Hendrik Reek, Amersfoort (NL)

(73) Assignee: BASF Nederland B.V. and University of Amsterdam, Florham Park, NJ (US)

( * ) Notice: Subject to any disclaimer, the term of this patent is extended or adjusted under 35 U.S.C. 154(b) by 101 days.

(21) Appl. No.: 12/162,166

(22) PCT Filed: Jan. 26, 2007

(86) PCT No.: PCT/NL2007/050033

§ 371 (c)(1),
(2), (4) Date: Nov. 24, 2008

(87) PCT Pub. No.: WO2007/086745

PCT Pub. Date: Aug. 2, 2007

(65) Prior Publication Data

US 2009/0082595 A1    Mar. 26, 2009

(30) Foreign Application Priority Data

Jan. 26, 2006   (EP) .................. 06075167

(51) Int. Cl.
*C07F 9/02* (2006.01)
*C07F 9/00* (2006.01)
(52) U.S. Cl. .............. 564/12; 564/14; 564/15
(58) Field of Classification Search ........... 564/12, 564/14, 15
See application file for complete search history.

(56) References Cited

U.S. PATENT DOCUMENTS 5,583,236 A    12/1996    Brush

FOREIGN PATENT DOCUMENTS

| EP | 1479439 | 11/2004 |
| WO | WO 00/55179 | 9/2000 |
| WO | WO2004/002995 | 1/2004 |
| WO | WO2005/063776 | 7/2005 |

OTHER PUBLICATIONS

Hopper, Darrin W. et al., "Facile Synthesis of Lysophospholipids Containing Unsaturated Fatty Acid Chains," Tetrahedron Letters, Oct. 28, 1996, vol. 37, No. 44, pp. 7871-7874.

Caturla, Francisco et al., "New fluorescent probes for testing combinatorial catalysts with phosphodiesterase and esterase activities," Tetrahedron, Feb. 16, 2004, vol. 60, No. 8, pp. 1903-1911.

Boruwa, J. et al., "Synthesis, absolute stereochemistry and molecular design of the new antifungal and antibacterial antibiotic produced by Streptomyces sp.201," Bioorganic & Medicinal Chemistry Letters, Jul. 5, 2004, vol. 14, No. 13, pp. 3571-3574.

Rohm and Haas, "Amberlyst A21 Industrial Grade Weakly Basic Polymeric Resin Product Data Sheet," Jul. 2005, rohmhaas.com/ionexchange/IP/literature.

*Primary Examiner*—Peter G O'Sullivan
(74) *Attorney, Agent, or Firm*—Raymond F. Keller

(57) ABSTRACT

The invention is directed to a process for the production of certain phosphorous, namely urea, thio-urea and sulphonamide phosphorous compounds. The present invention provides a process for the production of phosphorous compounds which process allows an easy and effective separation of the reaction products from impurities by applying a solid alkaline ion-exchange resin.

10 Claims, No Drawings

PROCESS FOR THE PRODUCTION OF PHOSPHOROUS COMPOUNDS

This application is a §371 national phase filing of PCT/NL2007/050033 filed Jan. 26, 2007, and claims priority to European Appln No. 06075167.4 filed Jan. 26, 2006.

The invention is directed to a process for the production of certain phosphorous compounds, namely urea phosphorous compounds, thio-urea phosphorous compounds, and sulphonamide phosphorous compounds.

These compounds are valuable for use in coordination complex systems comprising building blocks, such as the compounds described in WO-A-2004/103559.

The synthesis of phosphorous compounds, such as phosphites, is normally carried out by condensation of phosphor halides with organic compounds that carry hydroxyl groups in the presence of a base. The hydrogen halide which is formed during the reaction is captured by the base. Typically, the starting material is an organophosphorus chloride and the base is for instance trialkylamine such as triethylamine (TEA) or tributylamine, N,N-dialkylaniline or a nitrogen heterocycle such as pyridine. The hydrogen chloride will form an ammonium salt together with the base.

This formation of ammonium salts is particularly a serious problem in the synthesis of the urea, thio-urea and/or sulfonamide phosphorous compounds, especially in case the synthesis and the use thereof are in the context of robotic synthesis methods. It has been found, that the separation of the product from amine.HCl salts is particularly difficult for these types of phosphorous ligands.

Separation by distillation is often very hard and sometimes even impossible due to the low vapour pressure of the components involved. Chromatographic techniques are sometimes possible, but they are very time consuming are can decrease the yield substantially. Further, a problem exist in that this type of phosphite forms adducts with the amine.HCl salt, resulting in further difficulties with purification and loss of product. As a consequence, no commercially viable process was available for producing this type of phosphite. Object of the present invention is therefore to provide a process for the production of urea, thio-urea and/or sulfonamide phosphorous compounds that allows the production of said compounds, free from amine.HCl salts.

This object has been met by the process of the present invention for the production of a phosphorous compound having the structure

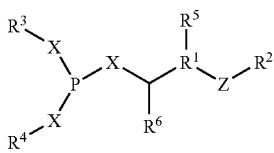

wherein X is O, N or C, $R^1$ is an alkylene moiety of 0 to 5 carbon atoms, $R^2$ is a hydrogen atom or a substituted or unsubstituted alkyl or aryl group, $R^3$, $R^4$, $R^5$ and $R^6$ are independently hydrogen or an optionally substituted aryl or alkyl group, and Z is at least one of

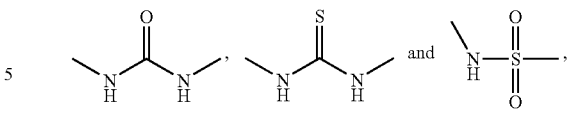

in which process

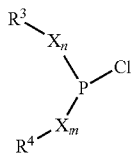

wherein X is O, N or C and n and m are independently 0 or 1, is reacted with $HY-C(R^6)-R^1(R^5)-Z-R^2$, wherein Y is O or NH, and Z is as defined above to produce the said phosphorous compound, in the presence of a solid alkaline ion-exchange resin.

Surprisingly, the inventors found that the phosphorous compounds of to the present invention can be synthesised in sufficient yield and substantially without adduct formation between ammonium chloride salts and phosphite by using a solid alkaline ion-exchange resin.

Moreover, the inventors found that the phosphorous compounds of the present invention are obtained in a pure form, without the need of further purification.

It is to be noted, that WO-A-2005/063776 describes a method for producing organophosphites by the condensation of phosphorus trihalides or organophosphorus halides with organic compounds that carry hydroxyl groups, in the presence of polymeric alkaline ion-exchange resins. The described method permits the production of trivalent organophosphorus compounds.

It is assumed that the reason for the problems in the synthesis of the urea, thio-urea and sulfonamide phosphorous compounds is that these phosphorous compounds are double hydrogen bonding donors and can for instance be used for the preparation of hydrogen bonded ligands for coordination compounds. In this case, the phosphorous compounds of the present invention bind to a hydrogen bonding acceptor through hydrogen bonds.

Due to this interaction the phosphorous compounds of the present invention are assumed to have a strong tendency to encapsulate the ammonium chloride salt in the final product. Due to the hydrogen bonding capability of the ureum, thioureum, and sulfonamide part of the phosphorous compounds, the TEA.HCl or other amine salts are assumed to be strongly bonded into clusters of phosphorous compounds, thereby making it virtually impossible through normal procedure to produce a sufficiently pure phosphorous compound, i.e. more than 95% pure, preferably more than 98% pure.

The use of a solid alkaline ion-exchange resin provides an immediate physical separation of the salts from the product; the product remains in solution. In a preferred embodiment, the liquid fraction of the reaction mixture is pumped to a second vessel over a filter. As a result, pure product is obtained in the second vessel while impurities of the mixture stay behind on the resin in the first vessel and cannot pass the filter.

The phosphorous compounds of the present invention have the following general formula.

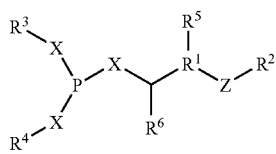

wherein X and Z have the above identified meanings.

$R^1$ is an optionally substituted aryl- or alkylene moiety. In a embodiment $R^1$ can be unsubstituted, but preferably $R^1$ is substituted with one or more alkyl- and or aryl groups. The aryl- or alkylene moiety of $R^1$ preferably has 0 to 6 carbon atoms, more preferably 2, 3 or 4 carbon atoms. The substituents can each contain 1 to 10 carbon atoms.

$R^2$ is an optionally substituted aliphatic, alicyclic, heterocyclic, or aromatic group. Combinations of these groups are also possible. $R^2$ preferably comprises from 1 to 50 carbon atoms. In case $R^2$ is substituted, one or more of the substituents may be for instance primary, secondary, or tertiary alkyl groups, alicyclic groups, aromatic groups, $-N(R^7)_2$, $-F$, $-Cl$, $-Br$, $-I$, $-CN$, $-C(O)-R^7$, $C(O)O-R^7$, $CF_3$, $-O-R^7$, $-C(O)N-R^7$, $-OC(O)-R^7$, or $-Si(R^7)_3$, wherein $R^7$ is hydrogen or a group comprising from 1 to 20 carbon atoms such as an alkyl group or an aryl group. $R^7$ is preferably a hydrogen atom or a methyl, ethyl, propyl, n-butyl, t-butyl, phenyl, or naphtyl group.

$R^3$, $R^4$, $R^5$ and $R^6$ are the same or different and are hydrogen or an optionally substituted aliphatic, alicyclic, heterocyclic, or aromatic group.

A preferred compound according to the invention is a compound of formula

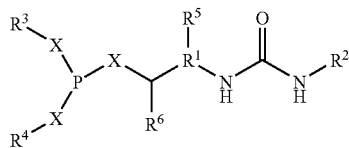

wherein X, $R^1$, $R^2$, $R^3$, $R^4$, $R^5$, and $R^6$ have the above identified meanings.

The reaction conditions of the process of the invention may vary with the substituents. However, typically the reaction is carried out at a temperature above −80° C., more preferably above −20° C. Degradation of the organic reactants and reaction products may occur when the reaction temperature is more than 180° C. Therefore, preferably the reaction is carried out at a temperature of from −20° C. to 50° C.

The reaction is typically carried out at a pressure of 1 bara.

Suitable solvents for carrying out the process of the invention include but are not limited to tetrahydrofuran, toluene and dichloromethane Preferred solvents are tetrahydrofuran and toluene. The exact choice of the solvent depends on the solubility of the reactants. The solvent should further be inert to the reactants. The person skilled in the art will be able to chose a suitable solvent based on the specific substituents of the reactants.

The process of the invention is preferably carried out under anhydrous conditions. This can be achieved by performing a two-fold azeotropic distillation of toluene from the reaction vessels prior to the reaction. In a special embodiment, the invention provides an efficient way of removing water during the reaction. A molecular sieve may be placed in a neighbouring vessel that is in open connection with the reaction vessel. The water evolved during the reaction is distilled with the toluene and is captured at the molecular sieves in the separate vessel.

The alkaline ion-exchange resin is preferably a weakly alkaline ion-exchange resin, based on amine groups. Preferably, the alkaline ion-exchange resin is based on organic polymers, which are effective in capturing the acid. Preferred ion-exchange resins are for instance based on amine base functionality. Preferably, commercially available ion-exchange resins of the AMBERLYST™ type are used.

The alkaline ion-exchange resin may be present in the form of particles. Preferably an ion-exchange resin is applied with a mean particle size of from 10 μm to 2 000 μm, more preferably from 100 μm to 1 500 μm, and most preferably from 400 μm to 1 000 μm. It is advantageous to use small particles of ion-exchange resin. A larger surface area of the particles is responsible for a faster capture of the hydrogen chloride formed during the reaction.

The minimum amount of alkaline ion-exchange resin to be applied can be calculated from the amount of reactants. Preferably, for each produced mol of acid, a free base is available in the ion-exchange resin. Most preferably 5 to 10 mol of free base is available for each mol of acid.

In a preferred embodiment, the reaction is carried out in a double vessel setup, wherein the reaction in the presence of the solid alkaline ion-exchange resin is performed in one vessel, while the ureum, thio-ureum and/or sulphonamide phosphorous product is collected in a connected second vessel after reaction. This allows for an easy and accurate separation of the final product by simply pumping the product mixture over a filter.

The molecules of the present invention contain a double hydrogen bond donor motive and can be coupled to molecules that contain hydrogen acceptors for example in order to form hydrogen bonded ligands for coordination compounds. Such coordination compounds may be used as transition metal catalysts. In order to screen a large library of coordination compounds for catalytic activity it is advantageous to simultaneously synthesise a range of different building blocks. It is therefore advantageous to produce the urea, thio-urea and/or sulfonamide phosphorous compounds of the present invention in a parallel synthesis procedure, wherein a multitude (for instance from 2 to 150) of different urea-phosphorous compounds are synthesised at the same time.

Such a parallel synthesis of phosphorous compounds is advantageously combined with robot synthesis, in which a series of parallel reactors are all connected to individual neighbouring vessels. By means of the robot system, series of 2 to 150 phosphorous ligands are synthesised in parallel followed by a parallel purification of all the products. The integration of a purification procedure in the robotic synthesis procedure greatly enhances the output of the parallel synthesis by avoiding tedious work-up procedures for all molecules produced.

Example Preparation of Phosphite

In a reactor block containing 16 reactors, in which two lines of reactors were connected in pairs, 8 simultaneous phosphite synthesis were performed in the reactors on the left-hand side. To this end ~0.5 mmol of the hydroxy-urea starting compounds were added to ~500 mg (5 equivalents) of Amberlyst A21. In two subsequent cycles, 2 mL of dry toluene was added to all 16 vials and evaporated under reduced pressure at 50° C. Next, 10 mL of tetrahydrofuran (THF) was added to the vials containing the reaction mixtures and the block was cooled down to 0° C. 0.9 equivalents of an 0.69 M R-Bisnaphtol-PCl solution in THF was subsequently added to the reaction mixtures upon vortexing at 1000 rpm. The mixtures were allowed to warm up to room temperature over 1 hour and were further vortexed at room temperature for 18 hours. All mixtures were then pumped to the vials on the right-hand side over PTFE filters (porosity G2/G3). After two washings of the solid bases with 2 mL of THF and pumping of the washings to the vessels on the right-hand side, the solvents were removed under reduced pressure at room temperature.

Details per vial:

|   | Hydroxy-urea | Weight (mg) | mmol |
|---|---|---|---|
| A | 1-(3-hydroxypropyl)-3-phenylurea | 94.4 | 0.45 |
| B | 1-butyl-3-(1-hydroxybutan-2-yl)urea | 72.0 | 0.35 |
| C | 1-butyl-3-(3-hydroxypropyl)urea | 94.1 | 0.54 |
| D | 1-(1-hydroxybutan-2-yl)-3-(4-methoxyphenyl)urea | 110.3 | 0.46 |
| E | 1-(1-hydroxypropan-2-yl)-3-(4-methoxyphenyl)urea | 89.9 | 0.40 |
| F | 1-(1-hydroxy-2-methylpropan-2-yl)-3-(3-methoxyphenyl)urea | 102.4 | 0.43 |
| G | 1-(1-hydroxypropan-2-yl)-3-(2-methoxyphenyl)urea | 104.0 | 0.46 |
| H | 1-(3-hydroxypropyl)-3-(2-methoxyphenyl)urea | 108.4 | 0.48 |

|   | Weight Amberlyst (mg) | mL bisnaphtol PCl solution |
|---|---|---|
| A | 459 | 0.59 |
| B | 357 | 0.46 |
| C | 551 | 0.70 |
| D | 561 | 0.71 |
| E | 392 | 0.52 |
| F | 439 | 0.56 |
| G | 469 | 0.60 |
| H | 493 | 0.63 |

|   | R-bisnaphtol-phosphite identification [$^{31}$P NMR] (ppm) | Yield (mg) |
|---|---|---|
| A | 140.6 | 73 |
| B | 142.9 | 32 |
| C | 141.1 | 124 |
| D | 141.0 | 145 |
| E | 140.6 | 116 |
| F | 144.0 | 73 |
| G | 140.2 | 51 |
| H | 141.0 | 45 |

The invention claimed is:

1. Process for the production of a phosphorous compound having the structure

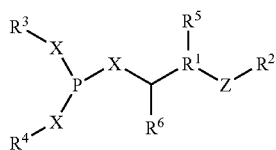

wherein X is O, N or C;
R$^1$ is an alkylene moiety of 0 to 5 carbon atoms;
R$^2$ is a hydrogen atom or a substituted or unsubstituted alkyl or aryl group;
R$^3$, R$^4$, R$^5$ and R$^6$ are independently hydrogen or an optionally substituted aryl or alkyl group; and
Z is at least one of

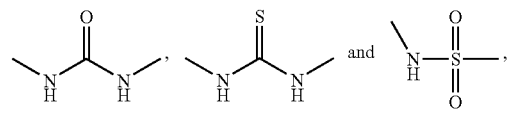

in which process

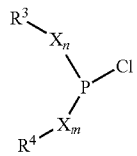

wherein X is O, N or C and n and m are independently 0 or 1, is reacted with HY—C(R$^6$)—R$^1$(R$^5$)—Z—R$^2$, wherein Y is O or NH, and Z is as defined above, to produce the said phosphorous compound, in the presence of a solid alkaline ion-exchange resin.

2. Process according to claim 1, wherein the alkaline ion-exchange resin is a weak alkaline ion-exchange resin, preferably based on amine groups.

3. Process according to claim 1, wherein the alkaline ion-exchange resin is present in the form of particles with a mean diameter of from 10 μm to 2 000 μm, more preferably from 100 μm to 1 500 μm, and most preferably from 400 μm to 1 000 μm.

4. Process according to claim 1, which process is carried out in a double vessel reactor, wherein the solid alkaline ion-exchange resin is present in one vessel and the product is collected in the other vessel.

5. Process according to claim 1, which process is carried out at a temperature of from −20° C. to 50° C.

6. Process according to claim 1, which process is carried out in a solvent chosen from the group consisting of tetrahydrofuran and toluene.

7. Process according to claim 1, wherein the process is carried out as a parallel synthesis of at least 2 different phosphorous derivatives.

8. Process according to claim 1, wherein R$^1$ is chosen from the group consisting of unsubstituted and substituted methylene, ethylene, propylene, butylene, wherein the substituted methylene ethylene, propylene, and butylene are preferably substituted with one or more alkyl- and or aryl groups that can contain 1 to 10 carbon atoms.

9. Process according to claim 1, wherein R$^2$ is chosen from the group consisting of phenyl, 2-methoxy phenyl, 3-methoxy phenyl, 4-methoxy phenyl, methyl, ethyl, propyl, n-butyl, and t-butyl.

10. Process according to claim 2,
wherein the alkaline ion-exchange resin is present in the form of particles with a mean diameter of from 10 μm to 2 000 μm, more preferably from 100 μm to 1 500 μm, and most preferably from 400 μm to 1 000 μm;
which process is carried out in a double vessel reactor, wherein the solid alkaline ion-exchange resin is present in one vessel and the product is collected in the other vessel;

which process is carried out at a temperature of from −20° C. to 50° C.;

which process is carried out in a solvent chosen from the group consisting of tetrahydrofuran and toluene;

wherein the process is carried out as a parallel synthesis of at least 2 different phosphorous derivatives;

wherein $R^1$ is chosen from the group consisting of unsubstituted and substituted methylene, ethylene, propylene, butylene, wherein the substituted methylene ethylene, propylene, and butylene are preferably substituted with one or more alkyl- and or aryl groups that can contain 1 to 10 carbon atoms; and wherein $R^2$ is chosen from the group consisting of phenyl, 2-methoxy phenyl, 3-methoxy phenyl, 4-methoxy phenyl, methyl, ethyl, propyl, n-butyl, and t-butyl.

* * * * *